(12) United States Patent
Maher

(10) Patent No.: US 11,224,533 B2
(45) Date of Patent: *Jan. 18, 2022

(54) CERVICAL COLLAR

(71) Applicant: Robert Michael Maher, Columbus, OH (US)

(72) Inventor: Robert Michael Maher, Columbus, OH (US)

(73) Assignee: NEURORESCUE, INC., Lafayette, LA (US)

( * ) Notice: Subject to any disclaimer, the term of this patent is extended or adjusted under 35 U.S.C. 154(b) by 352 days.

This patent is subject to a terminal disclaimer.

(21) Appl. No.: 16/528,090

(22) Filed: Jul. 31, 2019

(65) Prior Publication Data

US 2019/0350740 A1    Nov. 21, 2019

Related U.S. Application Data

(63) Continuation-in-part of application No. 15/287,227, filed on Oct. 6, 2016, now Pat. No. 10,426,658, which is a continuation-in-part of application No. 14/052,346, filed on Oct. 11, 2013, now Pat. No. 9,486,354, which is a continuation-in-part of application No. 13/309,173, filed on Dec. 1, 2011.

(60) Provisional application No. 61/419,018, filed on Dec. 2, 2010, provisional application No. 62/834,781, filed on Apr. 16, 2019.

(51) Int. Cl.
| | | |
|---|---|---|
| *A61B 5/01* | (2006.01) | |
| *A61F 7/02* | (2006.01) | |
| *A61F 5/055* | (2006.01) | |
| *A61F 7/10* | (2006.01) | |
| *A61B 5/00* | (2006.01) | |
| *A61F 7/00* | (2006.01) | |

(52) U.S. Cl.
CPC ............ *A61F 5/055* (2013.01); *A61F 7/0085* (2013.01); *A61F 7/02* (2013.01); *A61B 5/01* (2013.01); *A61B 5/4836* (2013.01); *A61B 5/6812* (2013.01); *A61B 5/6822* (2013.01); *A61B 5/742* (2013.01); *A61F 7/10* (2013.01); *A61F 2007/0009* (2013.01); *A61F 2007/0056* (2013.01); *A61F 2007/0095* (2013.01); *A61F 2007/0228* (2013.01)

(58) Field of Classification Search
CPC ..................................... A61F 7/0085
USPC ..... 602/14, 5, 1, 2, 18, 41, 60, 61; 607/109, 607/108, 96, 1, 104, 105
See application file for complete search history.

(56) References Cited

U.S. PATENT DOCUMENTS 9,486,354 B2 * 11/2016 Maher ................ A61F 7/10
10,426,658 B2 * 10/2019 Maher .................. A61F 5/055

* cited by examiner

*Primary Examiner* — Tarla R Patel
(74) *Attorney, Agent, or Firm* — Walter Haverfield LLP; James J. Pingor

(57) ABSTRACT

A cervical collar that facilitates therapeutic hypothermia is provided and includes a cooling device having a front portion and a back portion fixedly coupled to the front portion on one side and removably coupled to the front portion on an opposite side. A fastening device removably couples the back portion to the front portion on the opposite side. The cooling device induces hypothermia in at least a portion of a patient. A sensor is provided that measures a physical characteristic of the patient.

20 Claims, 14 Drawing Sheets

CERVICAL COLLAR

CROSS-REFERENCE TO RELATED APPLICATIONS

This application is a Continuation-in-Part of U.S. patent application Ser. No. 15/287,227 entitled "CERVICAL COLLAR" filed Oct. 6, 2016, which is a Continuation-in-Part of U.S. patent application Ser. No. 14/052,346, now U.S. Pat. No. 9,486,354, entitled "CERVICAL COLLAR" filed Oct. 11, 2013, which is a Continuation-in-Part of U.S. patent application Ser. No. 13/309,173, now abandoned, entitled "CERVICAL COLLAR" filed Dec. 1, 2011, which claims the benefit of U.S. Provisional Patent Application Ser. No. 61/419,018 entitled "CERVICAL COLLAR" filed on Dec. 2, 2010 and claims the benefit of U.S. Provisional Patent Application Ser. No. 62/834,781 entitled "CERVICAL COLLAR" filed on Apr. 16, 2019. The entirety of each of the above-noted applications is incorporated herein by reference.

ORIGIN

The innovation disclosed herein relates to a cervical collar and more particularly to a cervical collar employing a cooling device for therapeutic hypothermia.

BACKGROUND

A "neck brace" or "cervical collar" is a medical, and more particularly an orthopedic, device that is often used to support the cervical portion of a patient's spinal cord by immobilizing the head and neck region. These devices are often used by emergency medical technicians (EMTs), for example when responding to victims of traumatic head or neck injuries. Other uses of the devices include treatment of chronic medical conditions, sports injuries or the like.

Traumatic head or neck injury can expose a patient to extensive spinal cord injury which could escalate to full or partial paralysis, or even death. In an effort to minimize these risks and to stabilize the top vertebrae, EMTs, and other medical personnel, often position a cervical collar on patients as a precautionary measure. Additional stabilization methods can be accomplished by way of other devices such as a backboard. Other uses of the cervical collar are for treatment of injuries including, strains, sprains or whiplash.

The innovation disclosed herein is an improvement to the conventional cervical collars described above.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

In accordance one aspect of the innovation, a system that facilitates therapeutic hypothermia that includes a cervical/neck collar including an outer shell having a front portion and a back portion fixedly coupled to the front portion on one side and removably coupled to the front portion on an opposite side, and a bladder disposed on an interior of the outer shell, wherein the bladder selectively targets blood flowing through cerebral circulation arteries thereby changing a temperature of the blood flowing through the cerebral circulation arteries to a patient's brain.

In accordance with another aspect of the innovation, a system is disclosed that facilitates prevention of over-heating and/or comfort that includes a cervical/neck collar that includes an outer shell having a front portion and a back portion fixedly coupled to the front portion on one side and removably coupled to the front portion on an opposite side, a bladder configured to hold fluid disposed on an interior of the outer shell.

In accordance with another aspect of the innovation, a cervical collar is disclosed that includes an outer shell having a front portion and a back portion fixedly coupled to the front portion on one side and removably coupled to the front portion on an opposite side, a bladder configured to hold fluid disposed on an interior of the outer shell, and an indicator that changes color based on a change in a measurable event, wherein the bladder is the indicator.

In accordance with another aspect of the innovation, a cervical collar is disclosed that includes a bladder without an outer shell. In one aspect, the bladder may comprise an outer portion that is more rigid than an inner portion.

In accordance with still another aspect of the innovation, a method of targeted temperature management (e.g., inducing therapeutic hypothermia or warming) or increasing comfort is disclosed that includes placing a cervical/neck collar on a user's neck (e.g., a patient), circulating cooling or warming fluid through the collar, determining a differential threshold, measuring the patient's core temperature, measuring the patient's cerebral vasculature temperature, determining a difference between the patient's core temperature and the patient's cerebral vasculature temperature, comparing the difference to the differential threshold, and determining if the difference meets the differential threshold.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

Figure 1:
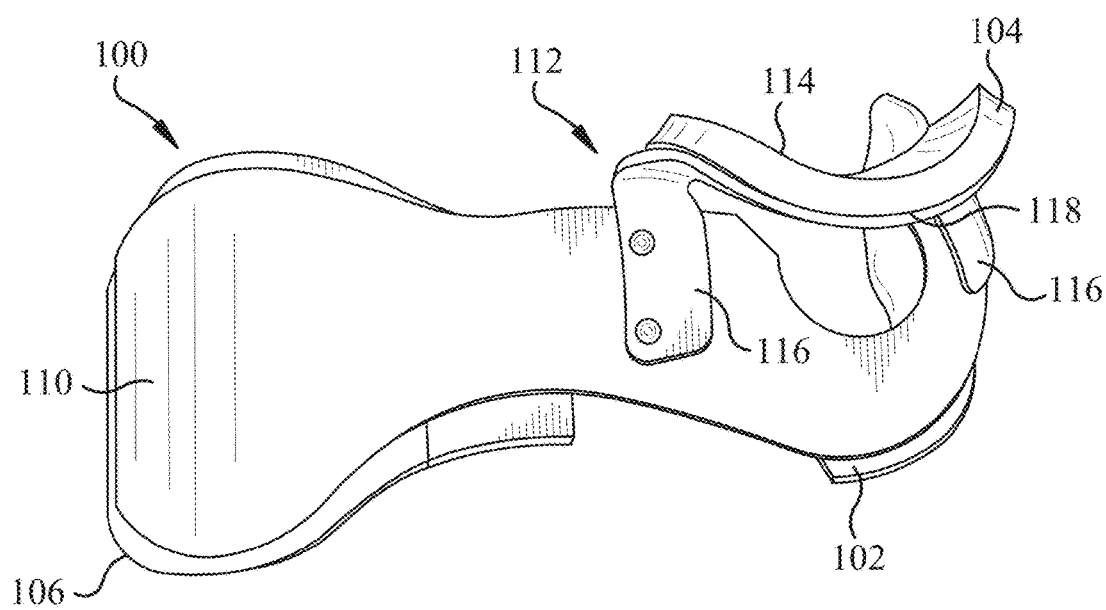
FIGS. 1 and 2 are exterior and interior views of a cervical collar incorporating a cooling device in accordance with aspects of the innovation.

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details.

While, for purposes of simplicity of explanation, the one or more methodologies shown herein, e.g., in the form of a flow chart, are shown and described as a series of acts, it is to be understood and appreciated that the subject innovation is not limited by the order of acts, as some acts may, in accordance with the innovation, occur in a different order and/or concurrently with other acts from that shown and described herein. Moreover, not all illustrated acts may be required to implement a methodology in accordance with the innovation.

Following is a discussion of the innovation and some example applications of the features, functions and benefits of employing a stabilizing device having a cooling (or warming device for certain medical applications) device as described herein. The innovation, in a broad application, is directed to the concept of induced or therapeutic hypothermia. Therapeutic hypothermia is a medical treatment for lowering one's core temperature to, for example, around 33° Celsius or other target temperature. Therapeutic hypothermia can be used to reduce the risk of tissue injury due to a period of insufficient blood flow caused by, for example, cardiac arrest or the occlusion of an artery by an embolism, as often occurs in the case of strokes. Studies have demonstrated, as is appreciated by those knowledgeable in the art that patients at risk for ischemic brain injuries have better results if treated with therapeutic hypothermia within the first sixty minutes, known as the "golden hour" by medical personnel, after the traumatic event.

Therapeutic hypothermia may be induced by either invasive or non-invasive procedures. Some non-invasive procedures may include packing or placing cold packs, cold compresses in the axil area, under the armpits or in the groin area to try to cool blood vessels. Another non-invasive procedure includes placing a chilled water blanket or torso vest and/or leg wraps in direct contact with the patient's skin. Some invasive procedures may include administering approximately 2,000 ccs (two bags) of a normal chilled saline solution, often referred to as a crystalloid, or placing a catheter in the inferior vena cava via the femoral vein.

The innovation disclosed herein enables pre-hospital care providers to get a thorough jumpstart of inducing therapeutic hypothermia through a non-invasive procedure. As used herein, pre-hospital care providers can include care administered by EMTs, paramedics, army medics, sports trainers, etc. In other words, the innovation can be employed by most anyone in the field. Similarly, the features, functions and benefits can be employed in a hospital or other medical care facility without departing from the spirit and/or scope of the innovation described herein. Thus, the innovation disclosed herein can be used by any type of medical personnel including those in the field or in a facility by a medical professional or caregiver.

While the innovation and the example embodiments described herein are directed to a cervical collar that includes a cooling device to target the carotid artery, it is to be appreciated that the features, functions and benefits of the innovation can be applied to other regions of the body for cooling or warming and for uses other than medical or therapeutic uses. Essentially, most any region whereby blood flows and can be affected by the cooling device of the cervical collar. In one embodiment, the cervical collar may act as a stabilizing device. For instance, areas where pulse points are located are most often good candidate regions for placement of the innovation. For example, in addition to the spinal/neck region, the innovation can be employed in the axil area, groin area, legs, arms, torso, etc. As will be understood, in order to enhance effects of cooling, it is important to cool as much blood as possible, thus, highly vascular regions are key regions for implementation, e.g., jugular veins, carotid arteries. In addition, it is to be understood that the innovation disclosed herein can also be used as a warming device. Thus, the innovation can be connected to a fluid source that can be used to circulate warming fluid through the innovation as described herein. Therefore, the example cervical collar disclosed herein is for illustrative purposes only and is not intended to limit the scope of the innovation.

In accordance with some aspects of the innovation, the innovation facilitates the placement of the cooling device in strategic anatomical positions on the neck region. Thus, the cooling device of the cervical collar can target the carotid arteries, which supplies the supply of blood flow to the brain, in the interior portion of the neck. In other aspects, the cooling device can target the posterior portion of the neck to cool the cervical areas of the neck to decrease swelling around the posterior portion of the neck including the spinal cord area and essentially cooling the neck as a whole. Thus, the cervical collar is capable of decreasing the temperature of the blood in highly vascular regions so as to enhance induced hypothermic reaction. More specifically, the cervical collar can selectively cool the cerebral vasculature relative to the whole body thereby inducing hypothermia. Because the cooling effect to the patient is targeted to a specific area (e.g., the brain), any side effects associated with whole body cooling are significantly reduced. Effectively, the cervical collar can most often be employed in three primary scenarios, stroke, heart attack, and head/neck injury or trauma.

It is to be understood that the innovation may be employed in non-medical and non-therapeutic scenarios. Reference to a "patient" is intended to include any user.

It is also to be understood that reference to a "cervical collar" is intended to include any device that can be worn around the neck to offer cooling/heating as described herein. It is intended that the terms "cervical collar," "cervical/neck collar" and "collar" be used interchangeably.

For example, the cervical/neck collar may be used to provide comfort or to prevent over-heating (e.g., heatstroke in, for example, a hot environment or during strenuous activities that include heavy equipment, such as military exercises/operations or athletics). It is further contemplated that a user may utilize the collar in situations where cooling would provide comfort. For example, the user may be outside on a hot day and may utilize the collar for purposes of comfort. It is also contemplated that the cervical collar could be used to prevent over-heating in situations where over-heating is suspected or possible. For example, during athletic events, a user may become over-heated or be in danger of becoming over-heated. In another example, the collar could be used by a first responder or soldier in situations involving extreme temperatures (hot or cold). The cervical collar could be employed prophylactically before signs of over-heating appear or could be employed once signs of over-heating appear so as to provide comfort and reduce the risks associated with over-heating.

It is also to be appreciated that any of the methods described herein are applicable to any user, whether for medical or non-medical purposes.

Figure 2:
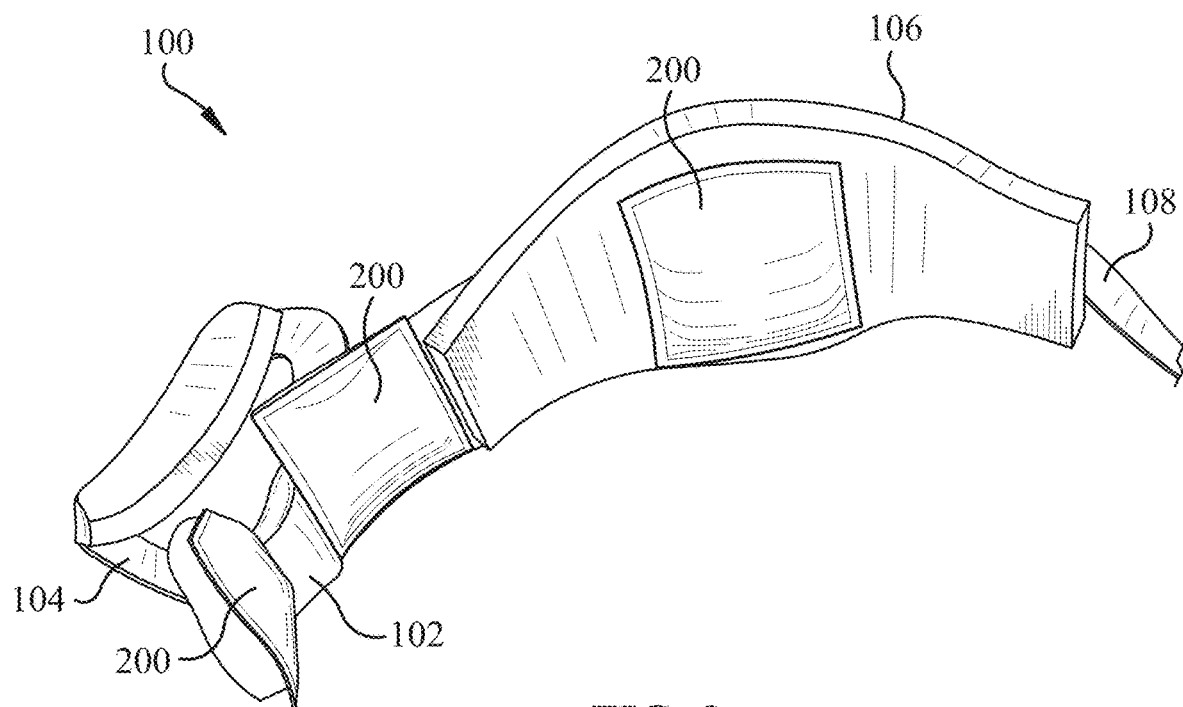

Referring now to the figures, FIGS. 1 and 2 illustrate an example embodiment of a stabilizing device, such as a cervical collar 100 that includes a cooling device in accordance with aspects of the innovation. The cervical collar 100 is most often used to immobilize one's neck in a trauma situation. The cervical collar 100 includes a front portion 102, an optional support 104 for supporting a patient's chin attached to the front portion 102, a back portion 106, and a fastening device 108 such as a strap. The fastening device 108 is attached to one side of the back portion 106 and extends toward the front portion 102. When the patient is wearing the cervical collar 100, the fastening device 108 removably attaches one side of the front portion 102 to thereby couple the front portion 102 to the back portion 106. The fastening device 108 may be any type of device, such as but not limited to a strap that employs a Velcro™-type fastener, snaps, buttons, hooks, etc. It is to be appreciated that most any means for attachment and/or adjustment can be employed in accordance with other aspects of the innovation. It is to be further appreciated that the fastening device 108 is adjustable to allow the cervical collar 100 to conform to patients having different sized necks.

It is to be appreciated that in some embodiments, the collar does not fully encircle a user's neck. In some embodiments, the collar may include a contiguous portion that is configured to securely fit around a user's neck without coupling a front portion and a back portion to encircle the user's neck. In some embodiments, the collar may have a generally U-shaped configuration.

The front and back portion 102, 106 are both made from a soft foam material that can be bent to conform to with the patient's neck, back, and shoulders. It is to be appreciated, however, that the front and back portion 102, 106 can be made from any suitable material as long as it conforms to the patient's neck, such as but not limited to, natural and synthetic polymers, carbon-reinforced materials, metal wire reinforced materials, etc.

It is to be appreciated that, while immobilization in specific scenarios (e.g., neck immobilization) is discussed in detail, the innovation and its features, functions and benefits can be used in other applications and scenarios without departing from the spirit and scope of the cooling effects described herein. In other words, it is to be understood that, while enhancing the cooling effects in response to an injury or condition, in accordance with some embodiments of the innovation need not also immobilize an injured area (e.g., the spinal area). These additional embodiments are to be included within the scope of the disclosure and claims appended hereto.

Referring specifically to FIG. 1, a flexible integrated outer shell 110 is attached to both the back portion 106 and the front portion 102 thereby coupling the other side of the front portion 102 to the other side of the back portion 106. The outer shell 110 can be attached to the front and back portion 102, 106 via any suitable means, such as but not limited to, an adhesive, rivets, etc. The outer shell 110 is flexible in a horizontal direction thus, allowing the cervical collar 100 to attach around the patient's neck. The outer shell 110, however, is more rigid in the vertical direction thus, giving the cervical collar its stabilization characteristics. In one embodiment, the outer shell may be flexible (e.g., not rigid in any direction) for circumstances where immobilization is not desired/warranted. The outer shell 110 can be any suitable rigid material or non-rigid material, such as but not limited to a molded plastic (e.g., polyethylene, polystyrene, etc.).

It is to be appreciated that, while a cervical collar having an outer shell is discussed in detail, the innovation includes embodiments wherein the cervical collar does not include a separate outer shell. In other words, the cervical collar may include a bladder (described more fully below) and does not include a separate outer shell. These embodiments are to be included within the scope of the disclosure and the claims as appended hereto.

Still referring to FIG. 1, the support 104 for supporting the patient's chin, also referred to as a chin cup, is attached to the front portion 102. It is to be appreciated that the support 104 is an optional device and the cervical collar 100 can still perform its intended function in accordance with aspects of the innovation without employing the support 104. The support 104 is disposed beneath the patient's chin for cervical support. The support 104 includes an attachment piece 112 that attaches to the front portion 102 and a rest piece 114. The attachment piece 112 includes two leg members 116 and a curved portion 118 connecting the two leg members 116. The leg members 116 are attached, via rivets or any other suitable means, to the front portion 102 to secure the support 104 to the cervical collar 100. The rest piece 114 is attached, via an adhesive or any other suitable means, to the curved portion 118 to support the patient's chin.

The support 104 can be fixedly attached or adjustably attached to the cervical collar 100. It is understood that individuals have different size necks and chins. Thus, in accordance with aspects of the innovation, the support 104 can be height (or otherwise) adjustable or interchangeable to facilitate comfort and enhanced immobilization effect. For example, in accordance with aspects of the innovation, the support 104 can be adjusted using a tongue and groove mechanism, where the support 104 can act like a tongue and the cervical collar 100 can employ the associated grooves. In accordance with other aspects of the innovation, the support 104 can include preselected heights. For example, a spring-button can be used that catches within a hole in the cervical collar 100 to secure the support 104 at a pre-selected height position. It is to be appreciated that other aspects can employ grooves, hardware (e.g., wing-nuts), etc. for adjustment without departing from the scope of the innovation. Thus, the adjustability of the support 104 and the cervical collar 100, via the fastening device 108, provides a universal fit and applicability of the innovation. Therefore, the cervical collar 100 is adjustable for both length (e.g., support 104) as well as width (e.g., fastening device 108).

In the examples illustrated below, the cervical collar 100 further includes a cooling device that may be in the form of a cooling pack (e.g., chemical pack) integrated into the cervical collar 100, a retainer to receive and hold a cooling pack (e.g., chemical pack, ice pack, sterile water cooling pack, etc.), or a bladder having chambers to allow cooling fluid to be pumped through essential portions of the cervical collar 100. It is to be appreciated that while pumping cooling fluid through the chambers of the bladder is described specifically herein, any method/means of causing cooling fluid to circulate throughout the bladder can be used without departing from the spirit and scope of the circulation of cooling fluid described herein. In other words, cooling fluid may be pushed and/or pulled to accomplish the desired circulation of cooling fluid.

While the embodiments described herein are generally related to fluids in a liquid state, it is to be appreciated that alternative aspects exist that employ other fluid states/phases such as air and gas to accomplish the features, functions and benefits described herein. These alternative embodiments are to be included within the scope of this specification and claims appended hereto.

The cervical collar 100 may optionally include features to permit access to areas of a patient for administration of medications or other treatments. For example, the cervical collar may include medical application openings within the outer shell. These openings may be strategically placed so as to permit access to specific regions (e.g., veins). In one embodiment, these openings may comprise perforated or otherwise removable portions to permit customized access according to need. For example, the medical application opening may comprise a portion of the cervical collar (e.g., the outer shell or the bladder if there is no outer shell) that is removable with force (e.g., pressure applied to a perforated region) to create medical application opening(s) only where needed.

In an alternate embodiment, at least a portion of the cervical collar (e.g., the outer shell or the bladder if there is no outer shell) comprises a penetrable material (e.g., able to be penetrated by medical equip such as a needle).

In yet another alternate embodiment, at least a portion of the cervical collar may include a movable portion to permit access. For example, the material may be arranged in overlapping slats wherein each slat is at least somewhat moveable so as to permit access for medical treatment (e.g., insertion of a needle for medication or an IV).

FIG. 2 illustrates one example embodiment of the cooling device in accordance with aspects of the innovation. The cooling device in this embodiment is a cooling pack 200 that can be either integrated into the cervical collar 100 or can be inserted into a retaining device described below. The cooling pack 200 can be strategically disposed at essential locations on the cervical collar 100 to target the areas of the neck described above. For example, one or more cooling packs 200 can be located on the front portion 102 to target the carotid arteries. In addition, one or more cooling packs 200 can be located on the back portion 106 to target the spinal cord area. The cooling pack 200 can be any type of cooling pack, such as but not limited to chemical pack (e.g., granule-activation packets that when activated releases a cooling agent to provide the desired cooling effect). For example, the granule-activation packets use ammonium nitrate and water. When a user strikes the cooling pack 200 with the palm of a hand, a prescribed amount of water will mix with the ammonium nitrate thereby creating a cold compress. Once the cooling packs 200 are activated, the cervical collar 100 can be placed on the patient to provide the desired therapeutic hypothermia to essential portions of the neck area described above.

The retaining device receives and holds a cooling pack, such as but not limited to, an ice pack or a chemical pack as described above. The retaining device can be strategically disposed at essentials locations on the cervical collar 100 to target the areas of the neck described above. For example, one or more retaining devices can be located on an interior side of the front portion 102 to target the carotid arteries. In addition, one or more retainers can be located on an interior side of the back portion 106 to target the spinal cord area. The retaining device can be in the form of a pocket, a pouch, straps, etc. and can be made from any suitable material, such as but not limited to, plastic, a mesh like material, etc. that sufficiently conducts the cooling effects of the cooling pack. It is to be appreciated that the options for the type and material of the retaining device are limitless and as such all of which are included in the scope of the innovation.

Figure 3:
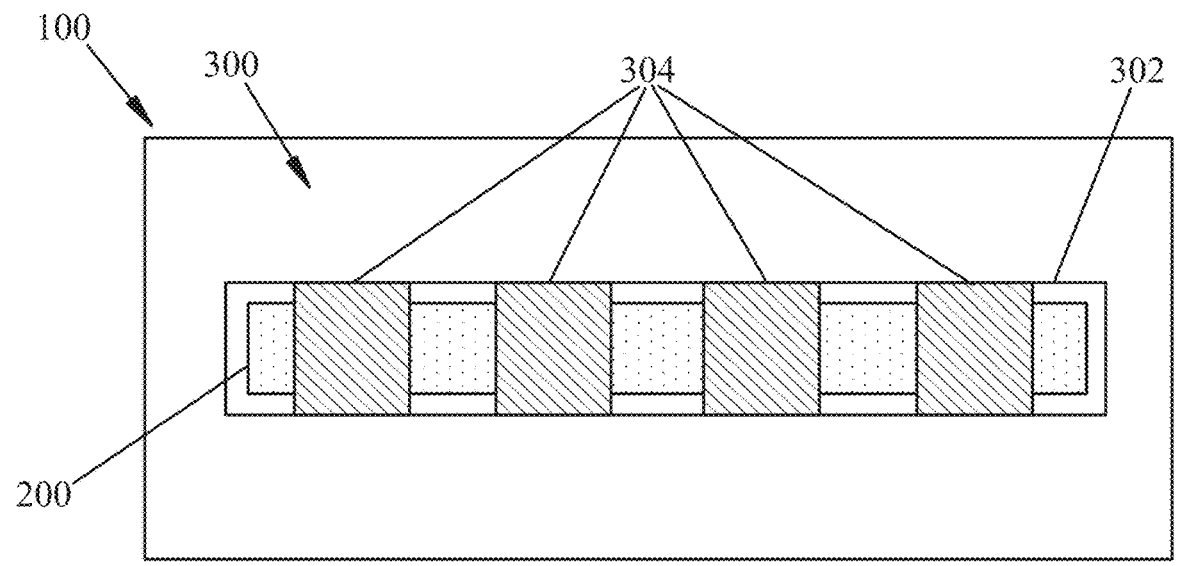
FIG. 3 is a block type diagram of the cervical collar of FIGS. 1 and 2 incorporating an example embodiment of the cooling device in accordance with aspects of the innovation.

For example, FIG. 3 is a block diagram illustration of the cervical collar 100 described above incorporating an example retaining device 300 in accordance with aspects of the innovation. The retaining device 300 includes a channel 302 and one or more covers 304 to hold the cooling pack 200 described above in place. The cover 304 may be made from any material that sufficiently conducts the cooling effects of the cooling pack 200 and that does not irritate the patient's skin. Further, the cover 304 can be a single piece or multiple pieces. In this embodiment, the cervical collar 100 can be packaged and transported in a flat condition to save space in transport vehicles such as emergency medical vehicles. When emergency personnel require the use of the cervical collar 100, the cooling pack 200 can be inserted or slid into the channel 302 and placed on the patient. When the cervical collar 100 is placed on the patient, the cooling pack 200 will activate thereby providing the required cooling effect. It is to be appreciated that the cooling pack 200 can be integrated into the channel 302 thus, saving the emergency personnel the time of placing the cooling pack into the channel 302. Once the cooling packs are secured by the one or more retaining devices, the cervical collar 100 can be placed on the patient to provide the desired therapeutic hypothermia to essential portions of the neck area described above.

Figure 4:
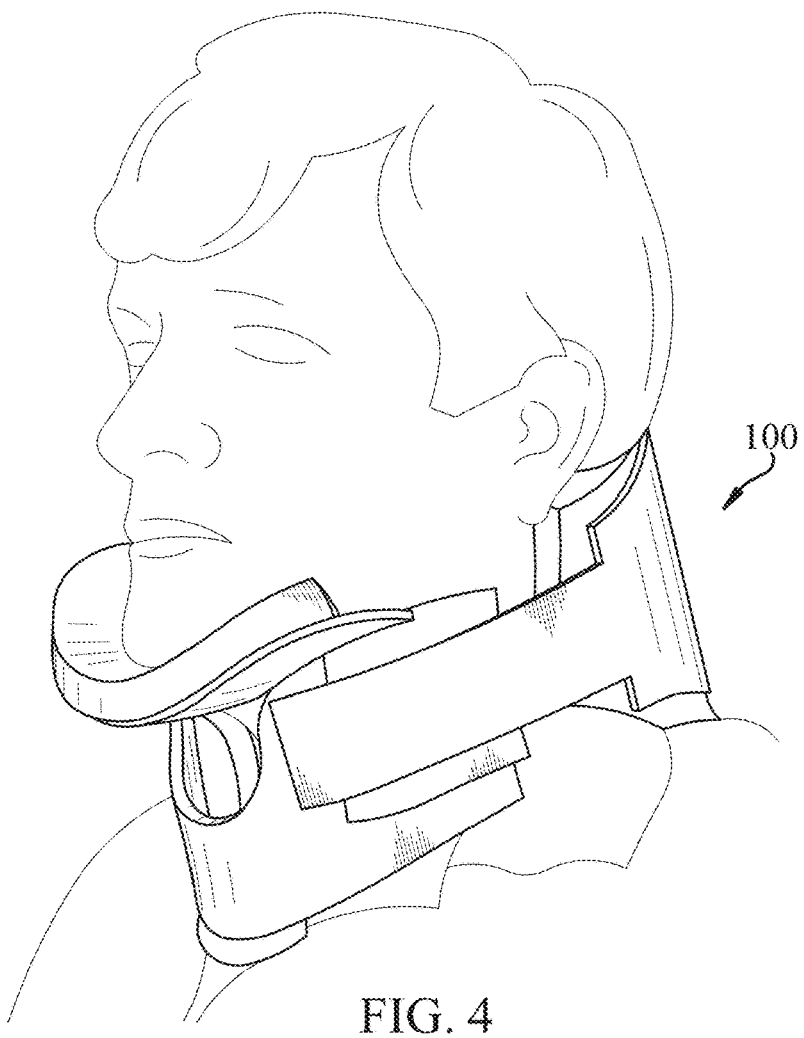
FIG. 4 is a perspective view showing the cervical collar of FIGS. 1 and 2 fitted to the patient in accordance with aspects of the innovation.

For example, FIG. 4 illustrates a perspective view of the cervical collar 100 described above fitted on a patient. As illustrated, the cervical collar 100 has the ability to provide therapeutic hypothermia upon vascular regions to facilitate promptly treating a patient and to minimize risk of further injury than that of conventional cervical collars.

FIGS. 5-8 represent another example embodiment of a cervical collar 500 (hereinafter "collar") incorporating a cooling/warming device. In this embodiment, the cooling/warming device allows cooling (or warming) fluid from an external fluid source, such as but not limited to, a portable fluid source or an external continuous fluid system to be squeezed or pumped into and/or circulated through essential portions of the collar 500. The collar 500 includes an outer shell 502, an adjustable support (not shown), and a bladder 506. It is to be appreciated that while the collar 500 can be used for inducing hypothermia, in some embodiments, the collar 500 can also be used for other purposes when a patient does not require therapeutic hypothermia. In one embodiment, the collar may be in fluid communication with additional cooling/warming devices such as a vest having a cooling/warming bladder or cooling/warming pouch. The vest may also be connected to a portable fluid source or an external continuous fluid system that is the same or different than the fluid source for the collar.

Figure 6:
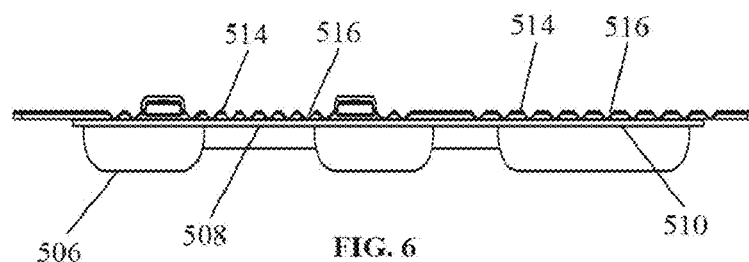
FIG. 6 is a top view of the cervical collar of FIG. 5 in accordance with aspects of the innovation.
Figure 7:
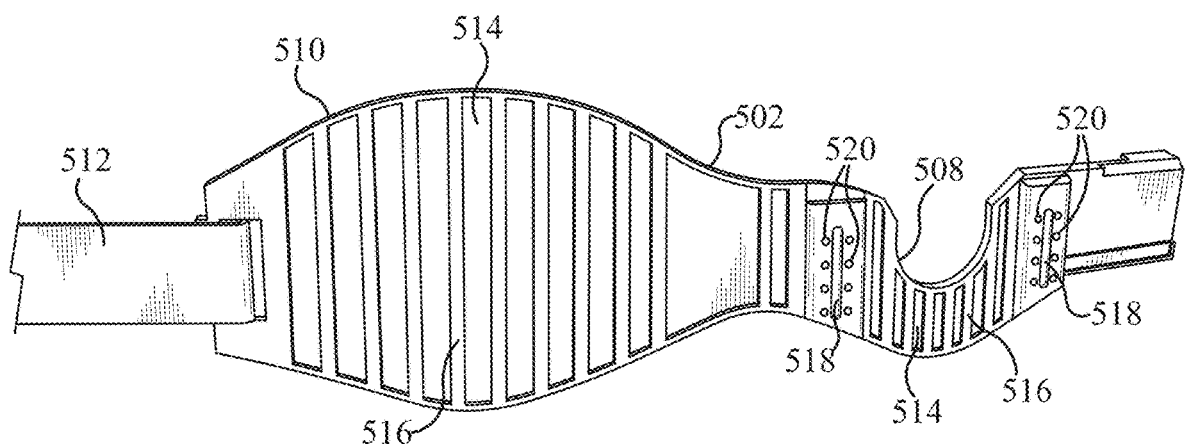
FIG. 7 is a rear view of the cervical collar of FIG. 5 in accordance with aspects of the innovation.

Referring to FIGS. 6 and 7, the outer shell 502 includes a front portion 508 fixedly coupled to a back portion 510 on one side and a fastening device 512 attached to the back portion 510 and removably coupling the front and back portions 508, 510 on an opposite side. The features of the fastening device 512 are similar to the fastening device 108 described above and, as such, will not be repeated.

The outer shell 502 is made from a flexible plastic material, such as but not limited to polyethylene, polystyrene, etc. Further, both the front and back portions 508, 510 include multiple panels 514 each connected by hinged portions 516 that further facilitate in the flexibility of the outer shell 502. This configuration allows EMT personnel to control the flexibility of the collar 500 and easily adjust the collar 500 to fit the patient. In addition, the flexibility characteristic allows the collar 500 to be packaged in a flat state thereby optimizing volume space for shipping and/or storage purposes. The front portion 508 of the outer shell 502 further includes multiple slots 518 and multiple recesses 520 disposed on each side of each slot 518. The multiple slots 518 and multiple recesses 520 facilitate attachment and adjustment of the support to the collar 500 subsequently described.

The support is used to support the patient's chin and is adjustable to conform to the patient similar to the support 104 described above. The support includes attachment legs that attach the support to the front portion 508 and a connection part connecting distal ends of the attachment legs. The connection part serves to support the patient's chin. Multiple slots 518 are defined in the front portion 508 to receive the attachment legs to thereby connect the support to the collar 500. The support can be adjusted by sliding each attachment leg in each slot 518 to a desired position. The attachment legs engage recesses 520 defined on each side of each slot 518 to lock the support in its desired position.

As mentioned above, the connection part provides a connection between the distal ends of the attachment legs. The connection point between the attachment legs and the connection part is hinged to facilitate packaging. Specifically, when the collar 500 is packaged in a flat state, mentioned above, one attachment leg is disconnected from the collar 500 and laid in a flat state. This is possible because of the hinged connection.

Figure 8:
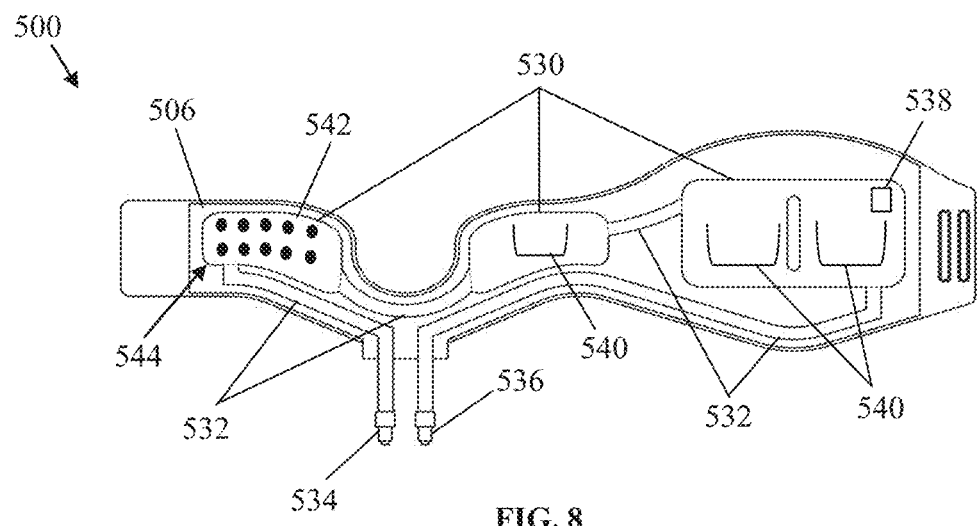
FIG. 8 is a front view of the cervical collar of FIG. 5 in accordance with aspects of the innovation.

Referring to FIG. 8, the bladder 506 is a single piece bladder type device that includes multiple cooling chambers (or reservoirs) 530, multiple passageways 532, an inlet port 534, and an outlet port 536. The passageways 532 provide a fluid connection between the chambers 530 and the inlet port 534, between the chambers 530 and the outlet port 536, and between the chambers 530 themselves.

The bladder 506 attaches to an interior portion of the outer shell 502 and can be made from multiple sheets of a flexible material that is conducive to conducting the cooling effects of the cooling, such as but not limited to, polyethylene. The multiple sheets can be arranged in numerous configurations, such as but not limited to, two sheets, three sheets, four sheets, etc. In instances where there are more than two sheets, multiple layers may be arranged on the patient side of the bladder 506 to facilitate the prevention of frost bite. The bladder 506 may be attached to the interior portion of the outer shell 502 by any suitable means, such as but not limited an adhesive.

As described above, in one embodiment, the cervical collar may not include a separate outer shell. The bladder may include a back portion (e.g., a patient side) and front portion. In one embodiment, the front portion of the bladder may comprise a more rigid material than the patient side. In one embodiment, the back portion may fixedly coupled to the front portion on one side and removably coupled to the front portion on an opposite side.

The chambers 530 are an integral part of the bladder 506. Specifically, to form the chambers 530, the two flexible sheets are placed in a heat mold and hermetically sealed in an area surrounding the desired location of each chamber 530. Although, the number of cooling chambers 530 illustrated in FIG. 8 is three, it is to be understood that the innovation is not dependent on the number of chambers 530 formed in the bladder 506. Thus, the example embodiment described herein and illustrated in the figures is for illustrative purposes only and is not intended to limit the scope of the innovation. It is to be appreciated, however, that the number and location of the chambers 530 targets essential areas of the patient's neck (e.g., carotid arteries, spinal area, etc.) to provide optimum cooling to the cerebral vasculature.

For example, the innovative cervical collar 500 may be configured to selectively cool or target cerebral circulation arteries, which are arteries that supply blood to the brain. More specifically, the cervical collar 500 may be configured to target arteries that supply blood to the anterior portion of the brain, known as anterior cerebral circulation. These arteries include the internal (intracranial) carotid arteries, external carotid arteries, anterior cerebellar arteries, anterior inferior cerebellar arteries, middle cerebral arteries, anterior spinal arteries, the anterior communicating arteries, and the ophthalmic arteries. The cervical collar 500 may also be configured to target arteries that supply blood to the posterior portion of the brain known as posterior cerebral circulation, including the occipital lobes, the cerebellum, and the brainstem. These arteries include vertebral veins and arteries including subclavian arteries, basilar arteries, posterior cerebral arteries, posterior cerebellar arteries, posterior inferior cerebellar arteries, posterior communicating arteries, pontine arteries, the superior cerebellar arteries, and the posterior spinal artery. In addition, the innovative cervical collar can also be configured to provide cooling to portions of the cranium, such as but not limited to the petrous bone.

As mentioned above, the passageways 532 provide a connection between the chambers 530, and between the chambers 530 and the inlet and outlet ports 534, 536. The passageways 532 may be comprised of embedded tubes or may be integrally formed in the bladder 506. Specifically, multiple tubes can be positioned at proper locations in the bladder 506 during formation of the chambers 530 described above, thus, embedding the tubes in the bladder 506. The passageways 532 may also be integrally formed in the bladder 506 by hermetically sealing an area surrounding each passageway 532 similar to the formation of the chambers 530 described above.

The inlet and outlet ports 534, 536 provide a connection between the bladder 506 and the external fluid system or source. The connection between the bladder 506 and the external fluid system or source can be any suitable mechanical connection device, such as but not limited to, quick couplers, a screw type device, etc. Further, the inlet and outlet ports 534, 536 may include a valve to regulate the flow of cooling fluid into and/or out of the bladder 506. It is to be appreciated that the inlet port 534 and the outlet port 536 can be switched. In other words, the inlet port 534 can serve as the outlet port 536 and the outlet port 536 can serve as the inlet port 534.

In one embodiment, the bladder may include multiple inlet and outlet ports configured to provide multiple connections between the bladder and an temperature modulation source (e.g., cooling or warming fluid).

Alternatively, still referring to FIG. 8, pockets or sleeves 540 may be attached to one or more chambers 530 that accept cooling packs 200 described above. The cooling packs 200 may be used in the event that the external fluid system of source is not available.

In still yet another embodiment shown in FIG. 8, one or more of the chambers 530 may include internal fasteners that connect a front 542 of the chamber to the back to thereby create a dimpled pattern 544. The dimpled pattern 544 flattens out the front surface 540 of the chamber 530 to allow more surface area to contact the patient. In addition, the internal fasteners cause the fluid inside the chambers 530 to flow in more a random pattern.

Figure 8A:
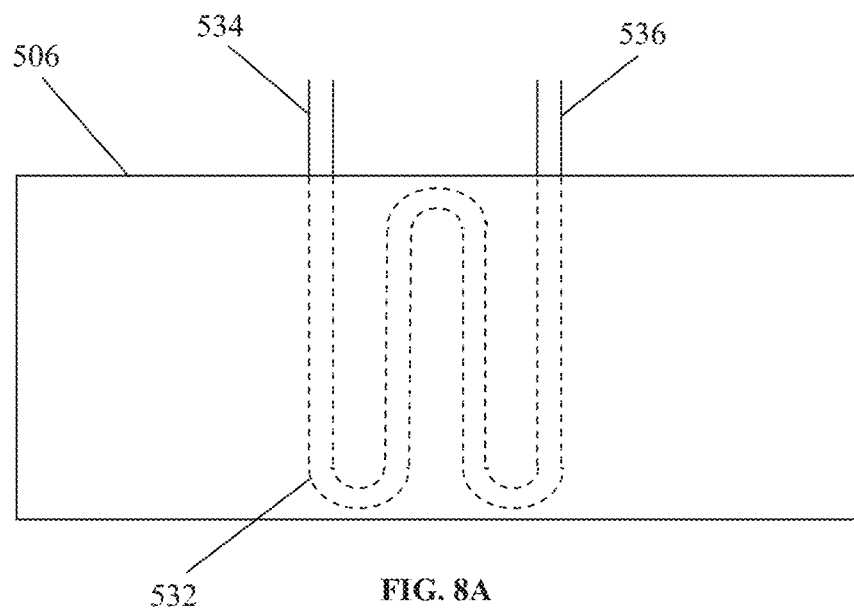
FIG. 8A is a block type diagram of another embodiment of a cervical collar incorporating a cooling device in accordance with aspects of the innovation.

In an alternative embodiment shown in FIG. 8A, the bladder 506 can be modified to exclude the chambers and simply include passageways 532 that run through the bladder 506 in desired locations. The passageways 532 would connect to both the inlet and outlet ports 534, 536 to allow the continuous circulation of cooling fluid, as described above.

Figures 9, 10:
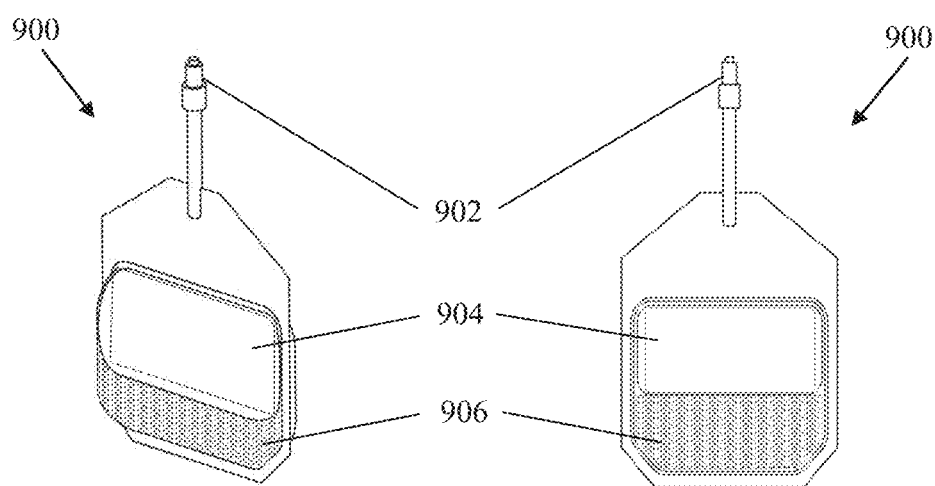
FIGS. 9-11 are perspective, front and side views respectively of a fluid source in accordance with aspects of the innovation.
Figure 11:
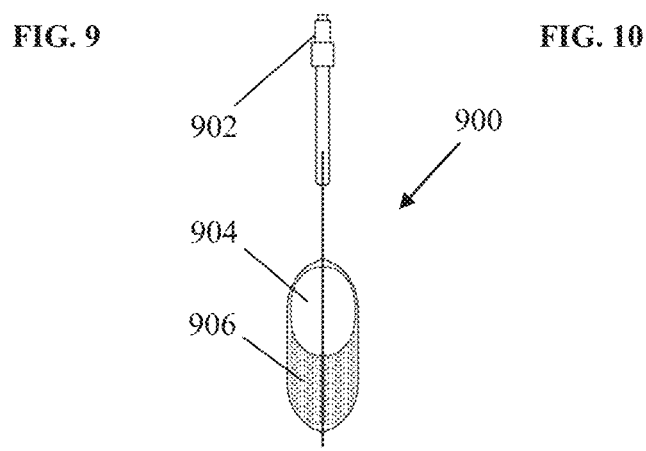

One such example of a fluid source is a portable cooling pack 900 illustrated in FIGS. 9-11. The portable cooling pack 900 includes a port 902 that acts as both an inlet port and an outlet port. The portable cooling pack 900 is a granule-activation packet that uses a fluid 904, such as but not limited to, water and a chemical 906, such as but not limited to, ammonium nitrate that when mixed together create a cooling fluid. When a user strikes the portable cooling pack 900 with the palm of their hand, a prescribed amount of water will mix with the ammonium nitrate thereby creating a cooling fluid. The cooling fluid from the portable cooling pack 900 can then be mechanically pumped or hand squeezed into the bladder 506 via the inlet port 534 and into each chamber 530 via the passageways 532, as described below.

In addition, once the cooling fluid inside the bladder 506 begins to warm, the empty cooling pack 900 can be attached to the outlet port 536 and a new portable cooling pack 900 can be attached to the inlet port 534. The cooling fluid from the new portable cooling pack 900 can then be pumped or squeezed into the bladder 506 thereby forcing or flushing the warm fluid out of the bladder 506 through the outlet port 536 and back into the original cooling pack 900. Thus, cooling fluid can essentially be continuously pumped through the collar 506 by EMT personnel who do not have access to a continuous external cooling system (described below) in the field. In addition, the fluid may be manually squeezed (or pumped) out of the bladder 506 such that the cervical collar 500 can function as a collar without the need to pump fluid through the bladder 506.

Figure 11A:
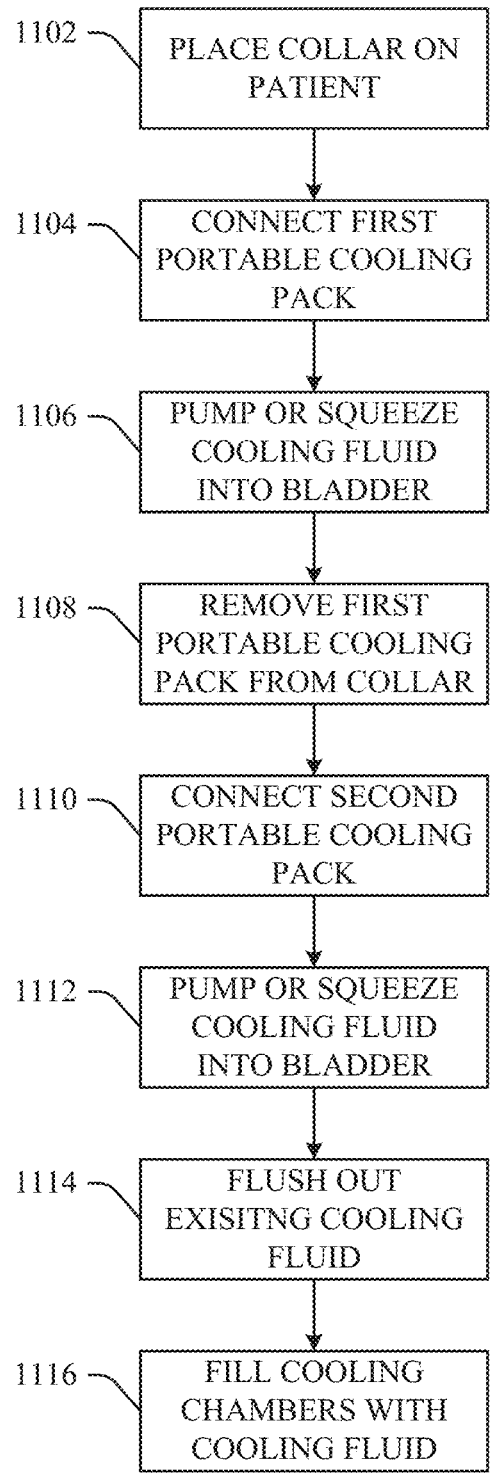
FIG. 11A illustrates a method of operating the cervical collar with portable fluid sources in accordance with aspects of the innovation.

For example, referring to FIG. 11A, at 1102, the cervical collar 500 is placed on the patient. At 1104, the port 902 of a first cooling pack is connected to the inlet port 534 of the cervical collar 500. At 1106, cooling fluid from the first cooling pack is squeezed into the bladder 506 of the cervical collar 500 thereby filling the cooling chambers 530. At 1108, once the cooling fluid from the first cooling pack reaches an undesirable temperature, the first cooling pack, which is empty, is attached to the outlet port 536 (or alternatively can be or stay connected to the inlet port 534). At 1110, a second cooling pack is attached to the port not in use (e.g., inlet port or outlet port) on the cervical collar 500. At 1112, cooling fluid from the second cooling pack is squeezed into the bladder 506. At 1114, the existing cooling fluid in the cooling chambers 530 from the first cooling pack is flushed out of the cooling chambers 530 and back into the first cooling pack. At 1116, cooling fluid from the second cooling pack fills the cooling chambers 530 with cooling fluid of a desired temperature.

In conjunction with the cooling packs 200, 900 previously described, the cervical collar 500 may include an indicator 538 (see FIG. 8) disposed on the retaining device 300 or on the bladder 506 (e.g., on at least one chamber 530 and/or at least one passageway 532) that indicates an approximate body (core) temperature of the patient and/or an approximate temperature of the patient's cerebral vasculature and/or an approximate temperature of the cooling fluid in the fluid source 200, 900. In one embodiment, the indicator 538 may be an integrated portion of the cervical collar 500. In another embodiment, the indicator 538 may be a separate temperature sensitive device (e.g., sticker, etc.) that can be attached to the cervical collar 500 by the EMT personnel. The separate temperature sensitive device may be removable and re-attachable so that it can be moved to different locations on the cervical collar 500.

In one example, the indicator 538 can sequentially change color based on a change of a measurable event, such as but not limited to a change in a temperature of the cooling fluid. For example, the indicator 538 may be a first color (e.g., blue, dark blue, etc.) when the temperature of the cooling fluid is at a temperature (first temperature) that provides adequate cooling to the patient. As the temperature of the cooling fluid begins to lose its cooling effect (e.g., the cooling fluid begins to warm) or approaches (or reaches) a second temperature, the indicator 538 may turn a second color (e.g., orange). The second temperature can be any temperature that is higher than the first temperature (e.g., "x" degrees warmer than the first temperature). As the temperature of cooling fluid continues to warm or approaches (or reaches) a third temperature the indicator 538 may turn a third color (e.g., red) indicating that the cooling fluid is no longer providing adequate cooling to the patient. The third temperature can be any temperature that is higher than the second temperature and obviously higher than the first temperature (e.g., "y" degrees warmer than the second temperature, "z" degrees higher than the first temperature). The indicator 538 can provide a quick visual means for the EMT personnel to determine if the cooling pack 200 should be replaced or if additional cooling fluid should be pumped into bladder 506 with another cooling pack 900.

Similarly, when the warm cooling fluid is flushed out and replaced with cold cooling fluid, the color of the indicator can change back to the first color (e.g., blue, dark blue, etc.). In addition, if the cooling fluid is gradually cooled from a warm temperature, the color of the indicator can change back in sequence toward the first color. As the cooling fluid once again begins to warm, the above process can start over again.

In another example embodiment, the indicator 538 can change color based on a change of a measurable event, such as but not limited to, a passage of time where specific colors may represent an incremental passage of time. For example, the indicator 538 may be a first color (e.g., blue, dark blue, etc.) when the cooling fluid is first introduced. As time passes (e.g., 1, minute, 2 minutes, 3 minutes, etc.) the indicator 538 may change color to a second color (e.g., orange) to alert the EMT personnel how much time has passed. As more time passes, the indicator may turn a third color, fourth color, fifth color, etc.

In one example embodiment, the color change may be gradual, which may represent a passage of time in small increments (e.g., 1 minute increments, 2 minute increments, etc.). In another example embodiment, the color change may be more defined or abrupt (i.e., changing quickly from one color to another), which may represent a passage of time in larger increments (e.g., 5 minutes, 10 minutes, etc.). For example in one embodiment, orange may represent the passage of 5 minutes, red may represent the passage of 10 minutes, etc. In another example embodiment, every time the indicator changes color may represent an incremental passage of time (e.g., any color change represents a 5 minute increment, a 10 minute increment, etc.).

In this example embodiment, the indicator 538 can provide a quick visual means for the EMT personnel to determine how much time has passed. Since time is very crucial in traumatic head and neck injuries, the quick reference indicator provides the EMT personal a means to quickly determine how much time has passed.

In another example embodiment, the bladder 506 or any portion thereof, such as one or more cooling chambers 530 or one or more passageways 532, may act as the indicator. For example, the bladder 506 may be made from a material that changes color based on temperature, as previously described.

In another example embodiment, the outer shell 502 may be made from a transparent material or may include a viewing window that permits the EMT personnel to view the patient's neck for signs of trauma and/or view the indicator 538 described above. In still another embodiment, the bladder 506 may be made from a transparent material that allows the EMT personnel to see the cooling fluid. As such, the cooling fluid itself may act as the temperature indicator. For example, a color of the cooling fluid may change color as the temperature of the cooling fluid changes, as described above.

Figure 12:
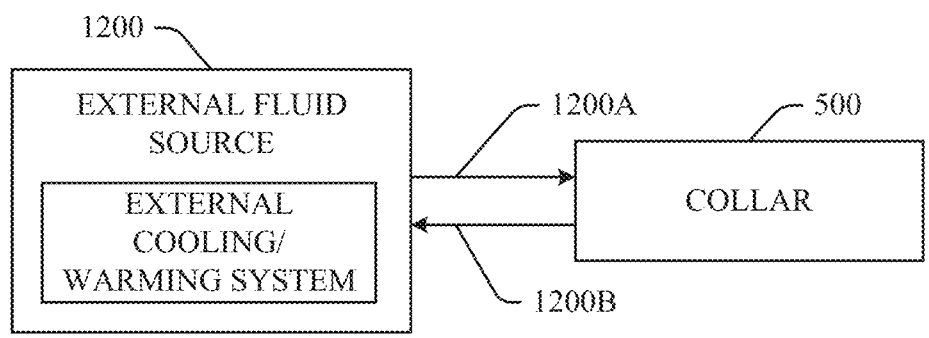
FIG. 12 is a block diagram illustration of an external fluid system fluidly communicating with the cervical collar in accordance with an aspect of the innovation.

Referring to FIG. 12, as mentioned above, another fluid source 1200 that the collar 500 can be connected to is an external cooling system 1200 that can continuously pump cooling fluid 1200A at a desired temperature through the bladder 506 thereby and flush out the warm cooling fluid 1200B, thereby providing a continuous circulation of cooling fluid at the desired temperature. Thus, the temperature of the cooling fluid can be regulated to maintain a predetermined temperature or adjust the temperature as desired. As such, this embodiment can be used to perform therapeutic hypothermia over an extended period of time to treat a particular type of injury or perform a particular type of procedure. For example, this example embodiment, as well as those described above, can be in the form of a wrap that employs the bladder 506 to treat injuries to the arms, shoulder, legs, knees, etc., as well as the neck area, where therapeutic hypothermia is required over an extended period of time.

Still referring to FIG. 12, it is to be understood that the innovative cervical collar disclosed herein can also be used as a warming device in appropriate medical applications. Thus, the cervical collar can be connected to the external fluid source 1200 that can pump warming fluid through the cervical collar as described herein. In one embodiment, the collar may be used for targeted temperature management in a hospital or medical environment. For example, the collar may be used to keep a patient warm during surgery or other medical procedure. In one embodiment, the collar may be used to modulate a patient's temperature post surgery. In one embodiment, the collar may be used for targeted temperature management in extreme environments, including in cold conditions.

Still referring to FIG. 12, the innovative cervical collar 500 can also be used as a compress. For example, in post-operative care, a practitioner can simply set the temperature of the fluid that does not induce hypothermia for the purpose of applying a cool or warm compress to the designated area. Still further, the practitioner can regulate the temperature of the fluid to transition between a cold compress and a warm compress and vice versa for therapeutic reasons.

Figure 12A:
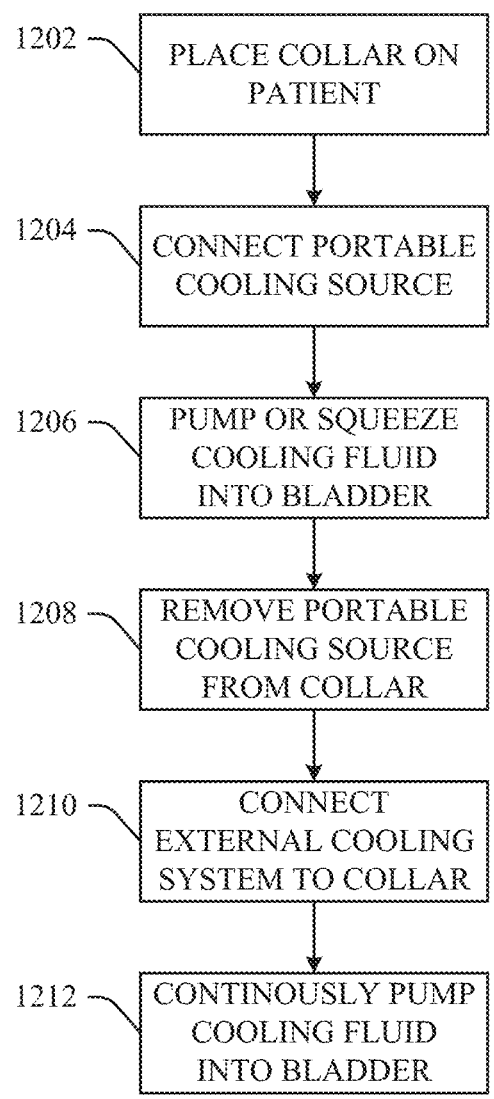
FIG. 12A illustrates a method of transitioning from a portable fluid source to an external fluid system in accordance with an aspect of the innovation.

In addition, referring to FIG. 12A, the external cooling system 1200 in conjunction with the cooling packs 900 can provide a smooth transition from providing portable cooling fluid in the field to a continuous cooling system in a medical facility. Thus, once the patient arrives at a medical facility the cooling source can be transitioned from the portable cooling pack 900 described above to the external cooling system 1200 as illustrated in FIG. 12A. Specifically, at 1202, the cervical collar is placed on the patient. At 1204, the portable cooling pack 900 is connected to the inlet port 534. At 1206, cooling fluid from the cooling pack 900 is pumped or hand squeezed into the bladder 506 thereby filling the cooling chambers 530. At 1208, once the patient arrives at a facility (e.g., medical facility) that has an external cooling system 1200, the portable cooling pack 900 is removed from the inlet port 534. At 1210, the external cooling system 1200 is connected to the cervical collar 500. At 1212, cooling fluid is pumped into the bladder 506, which flushes out the existing cooling fluid inside the cooling chambers 532.

It is to be understood that the transition process illustrated in FIG. 12A can also be from the continuous cooling system to the portable cooling packs. For example, if a trauma patient is connected to the continuous cooling system in a medical facility that is not capable of handling trauma patients, the patient can be transitioned from the permanent system to the portable cooling packs in order to transport the patient to a trauma facility.

Figure 5:
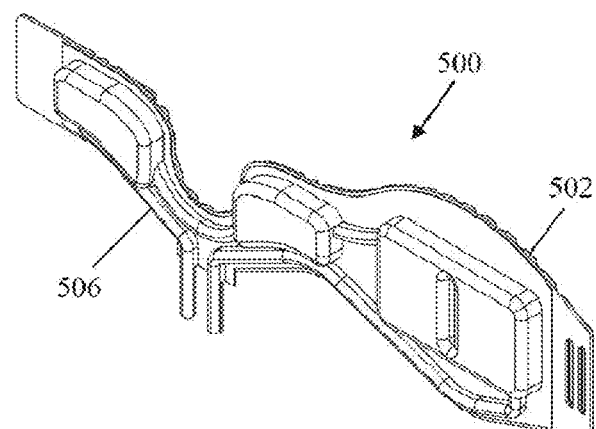
FIG. 5 is a perspective view of another embodiment of a cervical collar incorporating a cooling device in accordance with aspects of the innovation.
Figure 13:
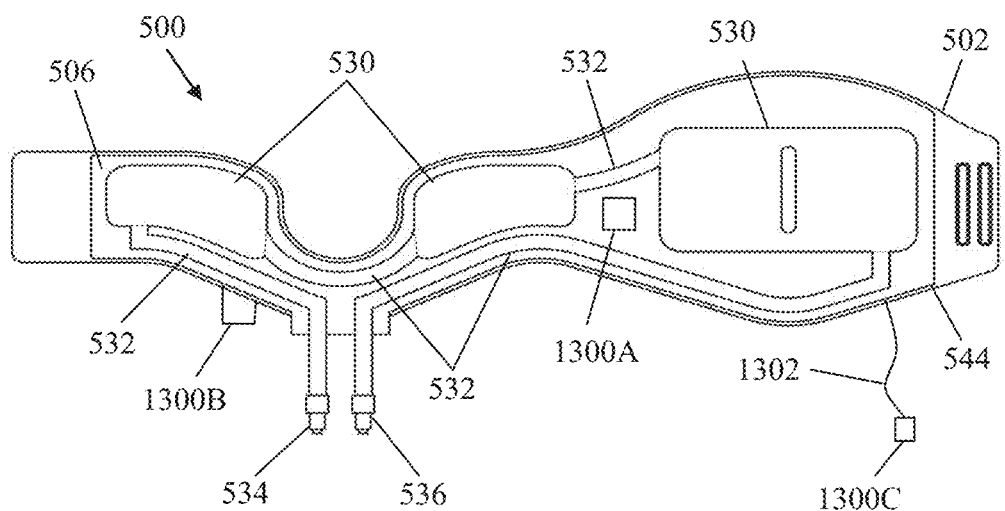
FIG. 13 is a front view of the cervical collar of FIG. 5 incorporating a temperature sensing device in accordance with an aspect of the innovation.

Referring to FIG. 13, the example embodiment of the cervical collar 500 illustrated in FIG. 5 above may include one or more temperature sensors 1300A or 1300B or 1300C that may measure a body (or core) temperature of the patient and/or a cerebral vasculature temperature of the patient. Although like features are referenced in FIG. 13, a description of such features will not be repeated for simplicity. The temperature sensors 1300A-C illustrated in FIG. 13 can be any type of temperature sensor, such as but not limited to, an infrared sensor, a stick tab sensor, etc. The presence of a temperature sensor allows medical personal to not only monitor, but also regulate the patient's body and/or cerebral vasculature temperature via the external cooling system mentioned above. Thus, to increase or decrease either temperature of the patient, the flow rate of the external cooling system is either increased or decreased respectively (alternatively, the temperature of the cooling can be adjusted as opposed to the flow rate). Thus, medical personnel are able to maintain the patient's body or cerebral vasculature temperature at a target temperature to thereby minimize the traumatic effect to the patient. It is to be understood, that any type of sensor that measures a physical characteristic of the patient may be included in the cervical collar. For example, in lieu of or in addition to a temperature sensor, a sensor may be included that measures the patient's pulse, etc.

In one example embodiment, the temperature sensor 1300A can be disposed on the bladder 506 such that when the cervical collar 500 is placed on the patient, the temperature sensor 1300A is already positioned to monitor the body temperature of the patient.

In another example embodiment, the temperature sensor 1300B can have a tab like configuration that attaches to a bottom edge 546 (as shown in FIG. 13) of the cervical collar 500. Thus, when the cervical collar 500 is placed on the patient, the temperature sensor 1300B is already positioned to monitor the body temperature of the patient. It is to be appreciated that the tab like temperature sensor 1300B can attach to a top or side edge of the cervical collar 500.

In still yet another example embodiment, the temperature sensor can be attached to any location (e.g., the outer shell 502, the bladder 506, etc.) on the cervical collar 500 via a tether 1302, as illustrated by temperature sensor 1300C. Once the cervical collar 500 is in place the temperature sensor 1300C can be placed on the patient at any convenient location, such as but not limited to, the forehead, neck area, etc.

Figure 14:
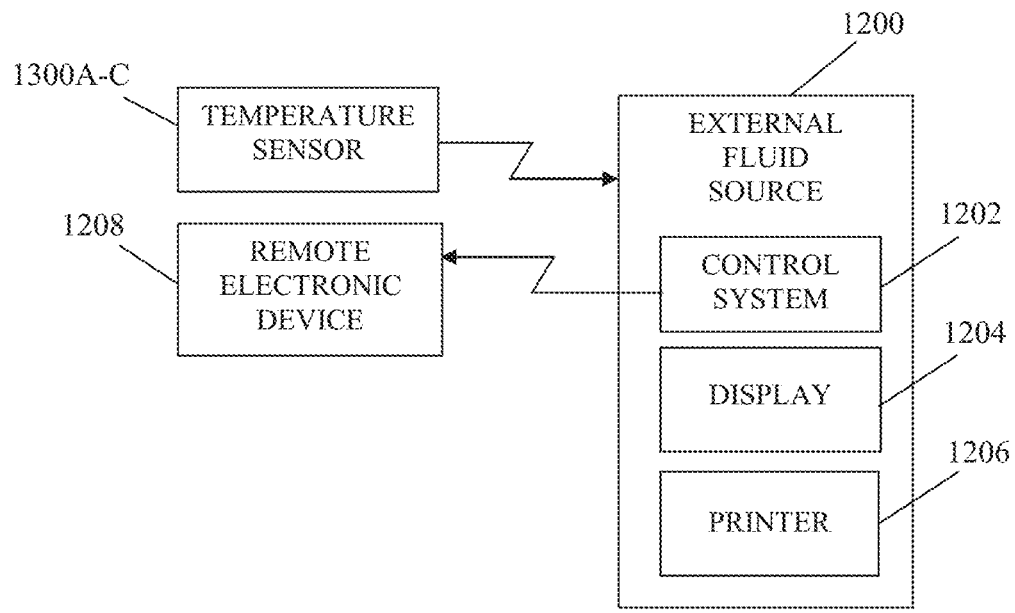
FIG. 14 is a block diagram illustration of the external cooling system communicating with peripheral electronic devices in accordance with an aspect of the innovation.

Referring to FIG. 14, in another embodiment, the temperature sensor 1300A-C can communicate with the external fluid source 1200 to automatically control the flow rate of the cooling fluid, thereby automatically adjusting the body temperature of the patient. For example, the body temperature of the patient can be continuously transmitted to a control system 1202 of the external fluid source 1200. The control system 1202 can then adjust the flow rate of the cooling fluid to adjust the body temperature until a desired target body temperature is reached. Further, the control system 1202 can continually or incrementally adjust the flow rate of the cooling fluid to gradually increase or decrease the patient's body temperature as desired.

In another example embodiment, the control system 1202 can be programmed to automatically adjust the flow rate of the cooling fluid to reach a target temperature based on several factors, including but not limited to, the patient's characteristics (e.g., the patient's health history if available, the patients physical make-up (e.g., height, weight, etc.)), environmental conditions (e.g., ambient temperature, etc.), etc.

Still referring to FIG. 14, patient information, such as but not limited to, patient's body temperature, flow rate of cooling fluid, patient's pulse, etc., may be visually displayed via a display 1204 associated with the external cooling system or printed via a printer 1206 associated with the external cooling system 1200. Further, the information may be transmitted from the control system 1202 to a remote location (e.g., medical facility) or to an electronic device 1408, such as but not limited to, a mobile phone, a tablet, a PDA, a computer, etc.

Figure 14A:
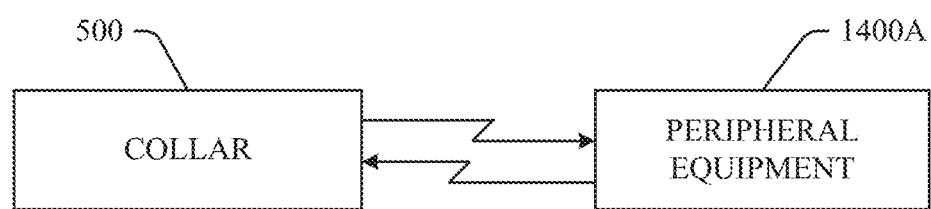
FIG. 14A is a block diagram illustration of the cervical collar communicating with peripheral electronic devices in accordance with an aspect of the innovation.

Referring to FIG. 14A, the innovative cervical collar 500 can be configured as part of a system that allows the cervical collar 500 to communicate with peripheral medical and non-medical equipment 1400A (e.g., fluid sources, thermal imaging devices (camera), temperature devices, printer, computer, etc.). Thus, the practitioner can program the peripheral equipment to set certain parameters. For example, the practitioner can program a temperature of the fluid, a flow rate of the fluid, a temperature of the patient's cerebral vascular and/or core, etc. Thus, the practitioner can easily achieve desired parameters by simply programming the peripheral equipment in use with the cervical collar 500. The communication between the cervical collar 500 and the peripheral equipment can be wired or wireless (e.g., RF, Bluetooth, etc.).

Figure 15:
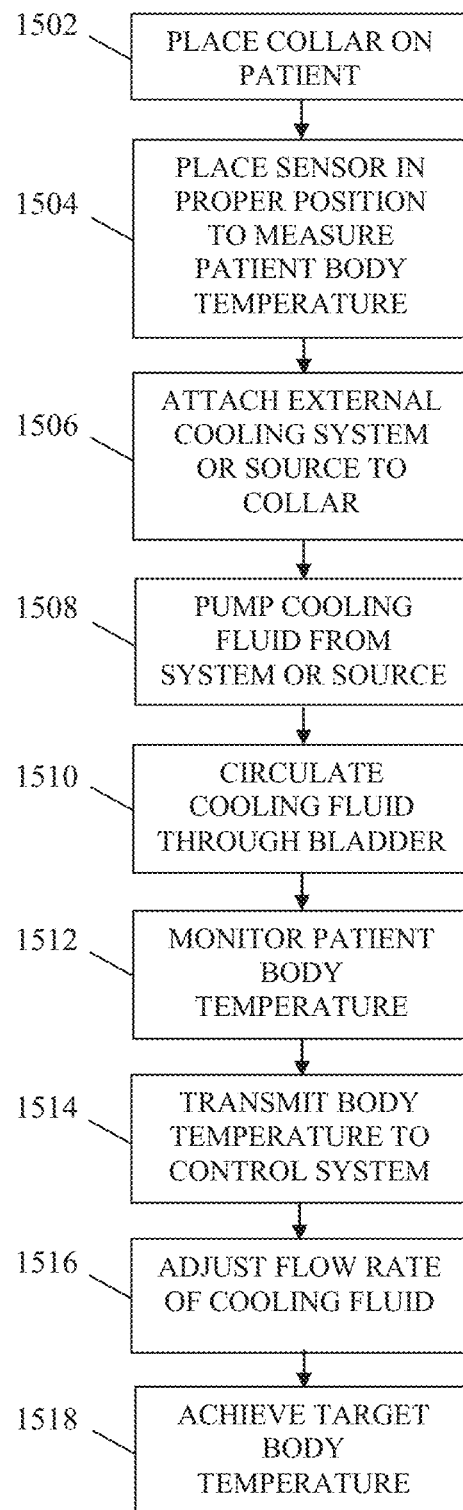
FIG. 15 illustrates a method of operating the cervical collar of FIG. 13 in accordance with aspects of the innovation.

Referring to FIG. 15, a method of using the collar 500 incorporating the bladder 506 will now be described. At 1502, the collar 500 is placed on the patient. At 1504, the sensor is properly placed to monitor the patient's temperature. At 1506, the external cooling system or source is connected to the bladder via the inlet and outlet ports 534, 536. At 1508, cooling fluid from the external cooling system or source is pumped into the bladder 506. If desired, at 1510, the cooling fluid can be continuously circulated through the bladder 506. At 1512, the patient's body temperature is monitored. At 1514, the body temperature is transmitted to the control system. At 1516, the flow rate of the cooling fluid is adjusted to regulate the patient's body temperature. At 1518, the target body temperature is achieved.

Figure 15A:
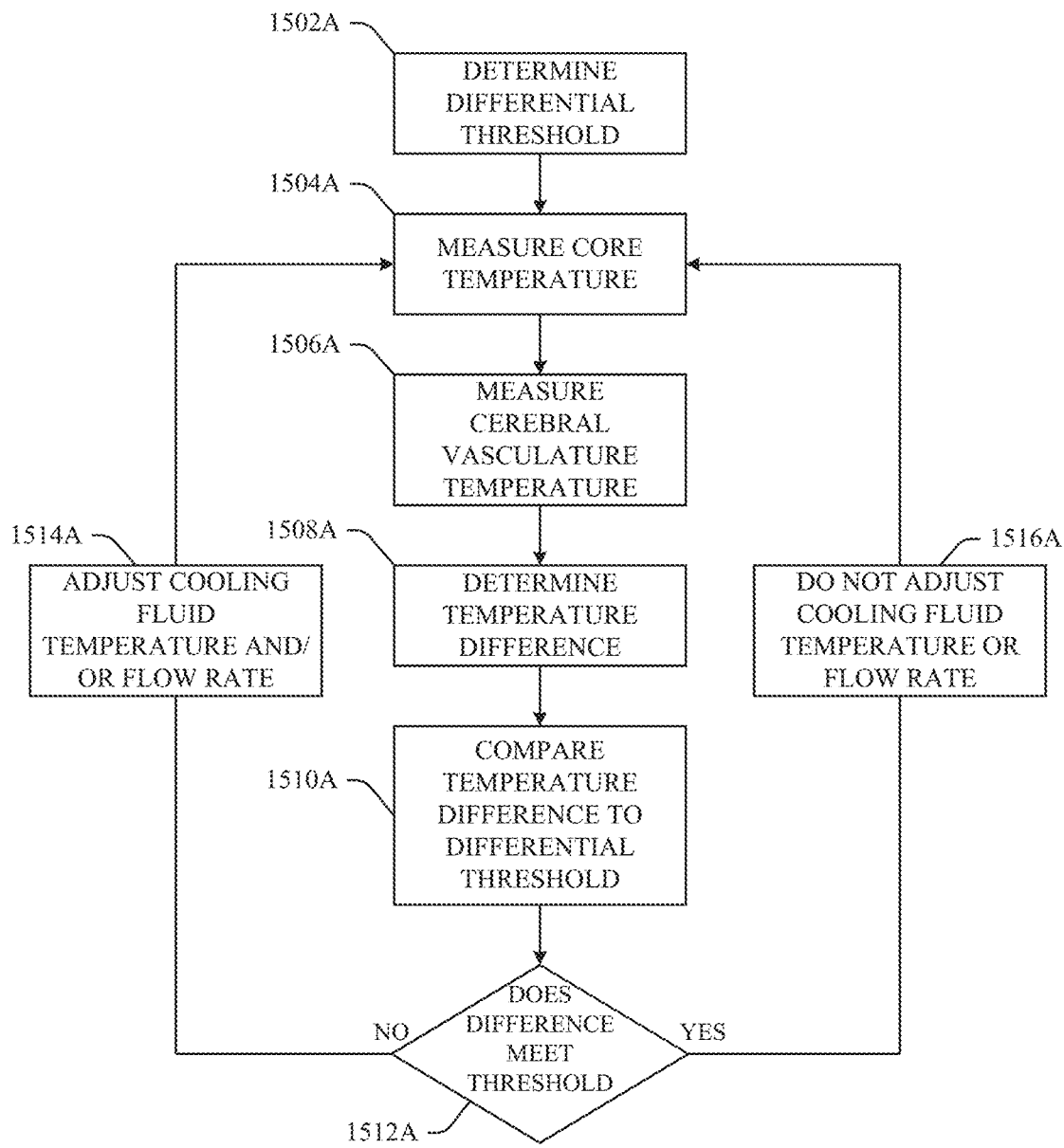
FIG. 15A illustrates a method of adjusting cooling fluid in the cervical collar in accordance with an aspect of the innovation.
Figure 16:
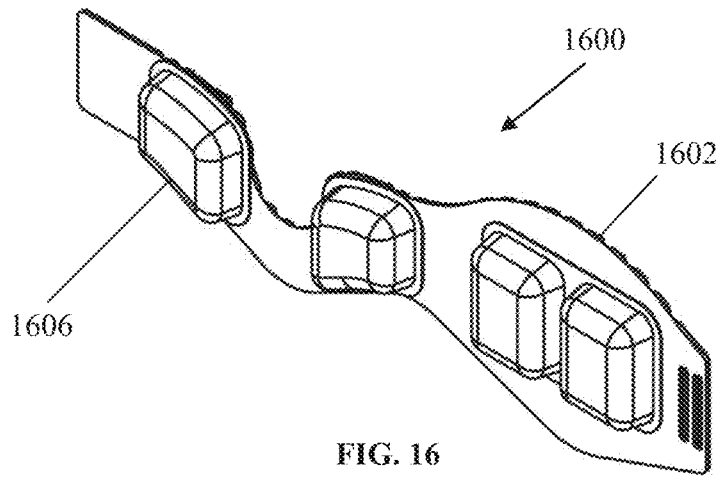
FIG. 16 is a perspective view of another embodiment of a cervical collar incorporating a cooling device in accordance with aspects of the innovation.

Referring to FIG. 15A, as mentioned above, in another example embodiment, the cervical collar 500 can include multiple temperature sensors to measure the patient's body (or core) temperature and the temperature of the patient's cerebral vasculature. The core temperature, the cerebral vasculature temperature, and/or the difference between the two can be used to determine if the temperature and/or flow rate of the cooling fluid should be adjusted. For example, once the cervical collar 500 is placed on the patient and the cooling fluid is circulating through the collar, at 1502A a differential threshold can be predetermined. At 1504A, the core temperature of the patient is measured and recorded. At 1506A, the temperature of the cerebral vasculature of the patient is measured and recorded. At 1508A, a temperature difference between the core temperature and the cerebral vasculature is determined. At 1510A, the temperature difference is compared to the differential threshold. If at 1512A the temperature difference does not meet the differential threshold, the process goes to 1514A and the temperature and/or the flow rate of the cooling fluid is adjusted. The process then loops back to 1504A and the process is repeated till the temperature difference meets the differential threshold. When the temperature difference meets the differential threshold then at 1512A, the process goes to 1516A and the temperature or the flow rate of the cooling fluid is not adjusted. The process then loops back to 1504A and the process is repeated to insure that the temperature difference continues to meet the differential threshold.

FIGS. 16-19 represent another example embodiment of a cervical collar 1600 (hereinafter "collar") incorporating a cooling device. The collar 1600 includes an outer shell 1602, an adjustable support (not shown), and a cooling device 1606. It is to be appreciated that while the collar 1600 can be used for inducing hypothermia, the collar 1600 can also be used as a standard cervical collar when a patient does not require therapeutic hypothermia.

Figure 17:
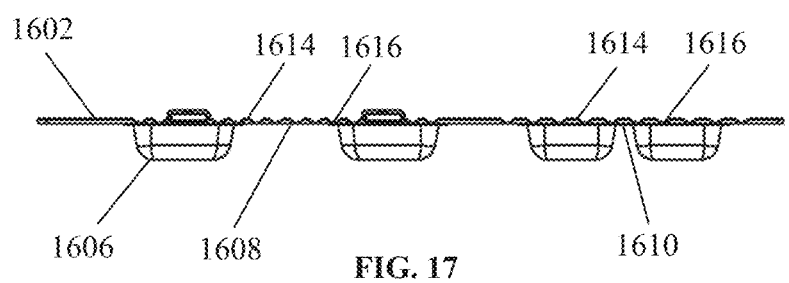
FIG. 17 is a top view of the cervical collar of FIG. 16 in accordance with aspects of the innovation.
Figure 18:
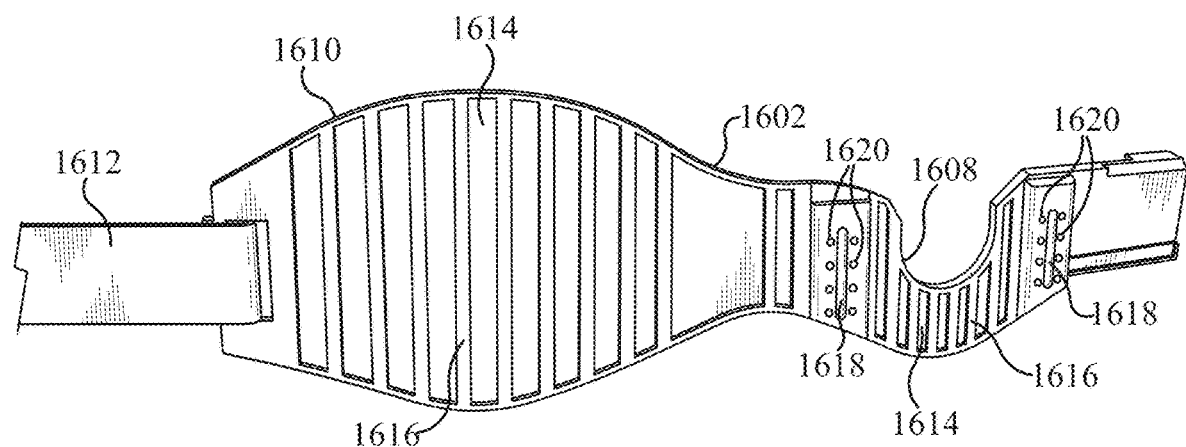
FIG. 18 is a rear view of the cervical collar of FIG. 16 in accordance with aspects of the innovation.

Referring to FIGS. 17 and 18, the outer shell 1602 includes a front portion 1608 fixedly coupled to a back portion 1610 on one side and a fastening device 1612 attached to the back portion 1610 and removably coupling the front and back portions 1608, 1610 on an opposite side. The features of the fastening device 1612 are similar to the fastening device 108 described above and, as such, will not be repeated.

The outer shell 1602 is made from a flexible plastic material, such as but not limited to polyethylene, polystyrene, etc. Further, both the front and back portions 1608, 1610 include multiple panels 1614 each connected by hinged portions 1616 that further facilitate in the flexibility of the outer shell 1602. This configuration allows EMT personnel to control the flexibility of the collar 1600 and easily adjust the collar 1600 to fit the patient. In addition, the flexibility characteristic allows the collar 1600 to be packaged in a flat state thereby optimizing volume space for shipping and/or storage purposes. The front portion 1608 of the outer shell 1602 further includes multiple slots 1618 and multiple recesses 1620 disposed on each side of each slot 1618. The multiple slots 1618 and multiple recesses 1620 facilitate attachment and adjustment of the support to the collar 1600 subsequently described.

The support is used to support the patient's chin and is adjustable to conform to the patient. The support includes attachment legs that attach the support to the front portion 1608 and a connection part connecting distal ends of the attachment legs. The connection part serves to support the patient's chin. Multiple slots 1618 are defined in the front portion 1608 to receive the attachment legs to thereby connect the support to the collar 1600. The support can be adjusted by sliding each attachment leg in each slot 1618 to a desired position. The attachment legs engage recesses 1620 defined on each side of each slot 1618 to lock the support in its desired position.

As mentioned above, the connection part provides a connection between the distal ends of the attachment legs. The connection point between the attachment legs and the connection part is hinged to facilitate packaging. Specifically, when the collar 1600 is packaged in a flat state, mentioned above, one attachment leg is disconnected from the collar 1600 and laid in a flat state. This is possible because of the hinged connection.

Figure 19:
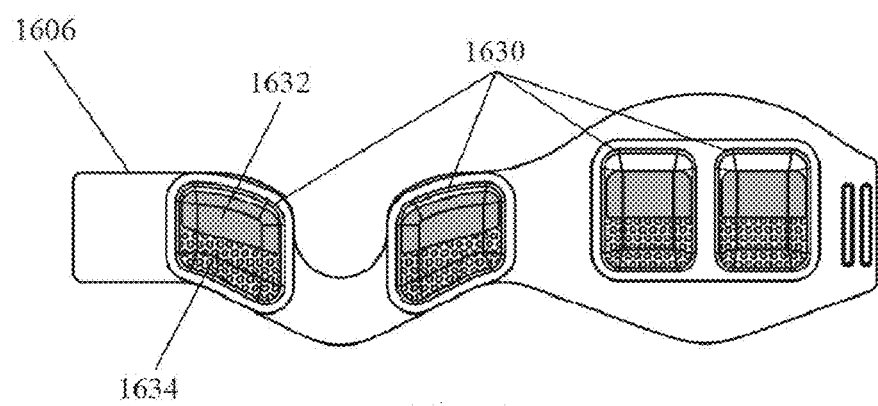
FIG. 19 is a front view of the cervical collar of FIG. 16 in accordance with aspects of the innovation.

Referring to FIG. 19, the cooling device 1606 includes one or more cooling packs 1630 integrated into an interior of the collar 1600. The cooling pack(s) 1630 can be strategically disposed at essential locations on the cervical collar 1600 to target the areas of the neck described above. For example, the cooling pack(s) 1630 can be located on the front portion 1608 to target the carotid arteries and/or on the back portion 1610 to target the spinal cord area. The cooling pack(s) 1630 can be any type of cooling pack, such as but not limited to chemical pack. For example, the cooling pack(s) 1630 can be a granule-activation packet uses a fluid 1632, such as but not limited to, water and a chemical 1634, such as but not limited to, ammonium nitrate that when mixed together create a cooling fluid. Once the cooling packs 1630 are activated, the cervical collar 1600 can be placed on the patient to provide the desired therapeutic hypothermia to essential portions of the neck area described above.

In other embodiments, the cervical collar disclosed herein can include a marking(s) and/or be made from different colors where the markings and/or colors represent a particular attribute. For example, the marking(s) and/or color may represent a type of injury that the cervical collar should be used on, a size of the cervical collar, a cooling fluid flow rate, if the cervical collar is used as a cooling device (e.g., the color blue) or used as a warming device (e.g., the color red), etc. In addition, the cervical collar may include multiple markings or different parts of the cervical collar may be made of different colors where certain combinations of markings and/or colors (e.g., the bladder may be one color and the outer shell may be a different color) represent one or more attributes of the cervical collar, such as those listed above.

For example, as mentioned above, the cervical collar can selectively cool the cerebral vasculature relative to the whole body. Thus, the cervical collar may include markings and/or be color coded to indicate that the cervical collar can be used to electively cool the cerebral vasculature. As medical professionals have a number of medical devices at their disposal, such as neck braces or other traditional cervical collars, the innovative cervical collar that includes markings and/or is color coded provides the medical professionals a vehicle to quickly identify the proper medical device required to treat the patient in circumstances where time is of the utmost importance.

As noted above, the innovation disclosed herein is not limited to a cervical collar to treat the neck area of a person. The innovation can be applied to any portion of the body that requires therapeutic hypothermia treatments. Thus, while a particular type of cooling device is described and illustrated, it is to be understood that alternative aspects can employ the cooling device without departing from the spirit and/or scope of the innovation.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A system that facilitates temperature modulation in a user comprising:
a neck collar including:
a bladder having a front portion and a back portion wherein the bladder comprises a plurality of chambers configured to retain fluid, and
a fluid source,
wherein the plurality of chambers are in fluid communication with the fluid source; and
wherein the bladder selectively targets blood flowing through cerebral vasculature thereby changing a temperature of the blood flowing through the cerebral vasculature of a user.

2. The system of claim 1, wherein the neck collar further comprises at least one passageway that fluidly connects the plurality of chambers with each other.

3. The system of claim 2, wherein the bladder further includes at least one inlet port and at least one outlet port connected to the at least one passageway that provide a connection between the fluid source and the plurality of chambers.

4. The system of claim 3, wherein the fluid source comprises a first portable temperature control pack comprising a temperature control fluid.

5. The system of claim 4, wherein the first portable temperature control pack is connected to the at least one inlet port and wherein the temperature control fluid may enter into the plurality of chambers via the inlet port.

6. The system of claim 5 further comprising a second portable temperature control pack, wherein the first portable temperature control pack is configured to be removed from the at least one inlet port after the temperature control fluid has entered the plurality of chambers and attached to the at least one outlet port and the second portable temperature control pack is configured to attach to the inlet port.

7. The system of claim 5, wherein the first portable temperature control pack is configured to be removed from the inlet port and wherein when the first portable temperature pack is removed, a continuous temperature control system is connected to the at least one inlet port and the at least one outlet port whereby temperature control fluid is continuously transferred through the bladder thereby transitioning the fluid source from the first portable temperature control pack to the continuous temperature control system.

8. The system of claim 7, wherein the continuous temperature control system is connected to the at least one inlet port and the at least one outlet port whereby temperature control fluid is continuously or selectively pumped through the plurality of chambers in the bladder.

9. The system of claim 8, wherein the continuous temperature control system is removeable from the at least one inlet port and the at least one outlet port and the first portable temperature control pack can be connected to the at least one inlet port.

10. The system of claim 4, wherein the first portable temperature control pack is a cooling or warming pack comprising a granule-activation packet.

11. The system of claim 4, wherein fluid from the portable fluid source may be mechanically pumped or manually squeezed through the inlet port of the bladder and into each of the plurality of chambers via the at least one passageway.

12. The system of claim 1, wherein the fluid source includes a port that acts as both an inlet port and an outlet port.

13. A neck collar comprising:
an outer surface having a front portion and a back portion;
a bladder disposed on an interior of the outer surface, the bladder comprising
at least one chamber configured to retain fluid;
an inlet port and an outlet port configured to create a fluid connection between the chamber and a portable fluid source,
wherein the bladder selectively targets blood flowing through cerebral vasculature thereby changing a temperature of the blood flowing through the cerebral vasculature to a user's brain.

14. The neck collar of claim 13, further comprising an indicator that changes color based on a change in a measurable event, wherein the bladder is the indicator.

15. The neck collar of claim 13, wherein the bladder comprises a plurality of chambers connected by a passageway, wherein the passageway provides a connection between the portable fluid source and the at least one chamber.

16. A method of modulating body temperature comprising:
placing a neck collar on a user's neck, the neck collar comprising a bladder configured to retain a fluid, wherein the bladder comprises at least one inlet port and at least one outlet port;
connecting a first fluid source to one of the at least one inlet port of the bladder;
circulating a fluid from the first fluid source through the bladder;
monitoring the temperature of the fluid inside the bladder;
disconnecting the first portable fluid source when the temperature of the fluid inside the bladder is outside a desired temperature range or threshold;
connecting a second fluid source to one of the at least one inlet port of the bladder; and
circulating a fluid from the second fluid source through the bladder.

17. The method of claim 16 further comprising:
determining a target core temperature and a target cerebral temperature for a user;
measuring the user's core temperature and cerebral temperature;
comparing the target core temperature to the measured core temperature;
comparing the target cerebral temperature to the measured cerebral temperature; and
adjusting the temperature or flow rate of the fluid if the measured core temperature or measured cerebral temperature is not in compliance with the target core temperature or target cerebral temperature.

18. The method of claim 16 wherein the first fluid source is a first portable fluid source and the second fluid source is a second portable fluid source.

19. The method of claim 18 further comprising activating the first fluid source such that activation of the first fluid source creates a cooling or warming fluid.

20. The method of claim 18 further comprising connecting the first portable fluid source to the outlet port of the bladder prior to circulating the fluid from the second portable fluid source, wherein circulating the fluid from the second portable fluid source causes fluid already within the bladder to be pushed into the first portable fluid source.

* * * * *